United States Patent [19]

Watts, Jr.

[11] 4,015,976
[45] Apr. 5, 1977

[54] N-ACETYL L-POLYCHLOROBENZAMIDE HERBICIDES

[75] Inventor: Lewis William Watts, Jr., Austin, Tex.

[73] Assignee: Texaco Development Corporation, New York, N.Y.

[22] Filed: June 26, 1975

[21] Appl. No.: 590,745

Related U.S. Application Data

[62] Division of Ser. No. 379,460, July 16, 1973, Pat. No. 3,959,370.

[52] U.S. Cl. .............................................. 71/118
[51] Int. Cl.$^2$ .......................................... A01N 9/20
[58] Field of Search ................................... 71/118

[56] References Cited

UNITED STATES PATENTS

| | | | |
|---|---|---|---|
| 2,937,204 | 5/1960 | Harris et al. ................. | 71/118 X |
| 3,439,018 | 4/1969 | Brookes et al. ............... | 71/118 X |
| 3,459,534 | 8/1969 | Dorfman et al. .............. | 71/118 |
| 3,751,239 | 8/1973 | McNulty et al. .............. | 71/118 |

*Primary Examiner*—Lewis Gotts
*Assistant Examiner*—Catherine L. Mills
*Attorney, Agent, or Firm*—James L. Bailey; John R. Kirk, Jr.

[57] ABSTRACT

Novel compounds, N-acetyl-polychlorobenzamides, are prepared by treating corresponding polychlorobenzonitrile compounds with acetic acid in a closed reactor at an elevated temperature above the boiling point of the acetic acid. These new compounds have been found to be useful biological chemicals, particularly in controlling undesirable vegetation, and also useful as chemical intermediates.

1 Claim, No Drawings

N-ACETYL L-POLYCHLOROBENZAMIDE HERBICIDES

This is a division of application Ser. No. 379,460 filed July 16, 1973, now U.S. Pat. No. 3,959,370.

BACKGROUND OF THE INVENTION

1. Field of the Invention

This invention pertains to new compositions of matter, their synthesis and biological use.

2. Description of the Prior Art

Wiley, R. H., and Guerrant, W. B., JACS, 71, 981 (1949) describe the formation of diamides from carboxylic acids and their nitriles. The reference discloses that heating together equimolar amounts of phenylacetic acid or p-nitrophenylacetic acid and their nitriles at temperatures up to about 250° C produces good yields of diamide. The reactions are carried out under oxygen free nitrogen to prevent discoloration and temperatures employed are below the atmospheric boiling point of the carboxylic acid reactants. However, the literature appears to be devoid of references to similar transformations of polyhaloaromatic nitriles, especially pentachlorobenzonitrile.

In a rather extensive investigation into the chemistry of pentachlorobenzonitrile and its derivatives, I have discovered that the reactions of these compounds are generally unpredictable. For example, there are classical methods known in the art to effect the conversion of nitrile derivatives to amide derivatives, such as mixing and reacting a nitrile with hot caustic, hot alcoholic caustic, mixtures of phosphoric and acetic acids, and the like. However, experiments have shown that the classical methods fail to effect the conversion of polychlorobenzonitrile derivatives to corresponding polychlorobenzamide derivatives, especially pentachlorobenzonitrile. Only a single example is known wherein a reagent attacks the cyano group. As described in my copending application, "Novel Process for Preparing Polyhalobenzamide Derivatives", Ser. No. 379,545, filed concurrently herewith, now abandoned. I have found that the treatment of polychlorobenzonitrile derivatives, especially pentachlorobenzonitrile and hydroxy-tetrachlorobenzonitrile, with concentrated sulfuric acid at elevated temperatures produces a resultant corresponding polychlorobenzamide derivative in near quantitive yields.

It was quite surprising, in view of these facts, to discover that N-acetyl-polychlorobenzamide compounds are produced by the treatment of corresponding polychlorobenzonitrile derivatives with acetic acid in a closed reactor at an elevated temperature above the atmospheric boiling point of the acetic acid at autogenous pressure. This was especially surprising in view of my observations that treatment of pentachlorobenzonitrile with a mixture of acetic and phosphoric acids produces no reaction products and that the treatment of pentachlorobenzonitrile with sodium acetate results in aromatic nucleophilic substitution with the cyano group being unreacted. That is to say, as also disclosed in my abovementioned copending application Serial No. (AL-1966) experiments have shown that the treatment of pentachlorobenzonitrile with sodium acetate at elevated temperatures results in the production of acetoxy-tetrachlorobenzonitrile which is essentially converted to the free acid form hydroxy-tetrachlorobenzonitrile by acid addition. In fact, as more particularly described hereafter, the novel compound N-acetyl-pentachlorobenzamide was first discovered in an attempt to produce chlorine-substituted acetoxybenzonitriles. In carrying out the experiment a mixture of pentachlorobenzonitrile, sodium acetate, acetic anhydride and acetic acid was heated in a sealed vessel at a temperature above the boiling point of the acetic acid. Most unexpectedly, analysis of the resulting isolated precipitate showed that it was N-acetyl-pentachlorobenzamide.

SUMMARY OF THE INVENTION

Novel compounds of the formula

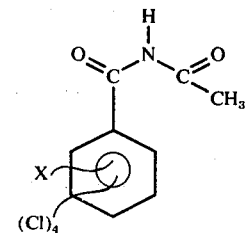

wherein X is a chloro or hydroxyl group have been found to be useful as highly effective herbicides. The compounds are prepared by mixing and reacting the corresponding polychlorobenzonitrile derivatives with acetic acid in a closed reactor at autogenous pressure and elevated temperatures above the atmospheric boiling point of the acetic acid for a time period sufficient to effect conversion thereof.

DESCRIPTION OF THE PREFERRED EMBODIMENTS

The novel compounds of my invention are prepared by mixing a polychlorobenzonitrile compound and acetic acid and allowing the compounds to react by heating the admixture in a closed reactor, such as a closed pressure vessel, under autogenous pressure and at an elevated temperature above the boiling point of the acetic acid at atmospheric pressure. Examples of polychlorobenzonitrile compounds useful in my invention include pentachlorobenzonitrile and hydroxy-tetrachlorobenzonitrile. Under normal atmospheric pressure, acetic acid normally will boil at about 118° to 120° C. Although any desired pressure can be employed, I prefer to carry out the inventive process at autogenous pressure. Under these conditions, the reactants are mixed at atmospheric pree and allowed to react in the closed reactor under autogenous pressure produced by the vapor pressure of the boiling acetic acid.

It is most critical in the practice of the present invention to employ an elevated temperature above the atmospheric boiling point of the acetic acid since experiments have shown that heating the reaction compounds at a lower temperature do not produce the novel compounds of the invention. Preferably, the mixture of polychlorobenzonitrile compound and acetic acid is heated in the closed vessel at an elevated temperature of between about 150° to about 250° C. An expecially preferred temperature range is between about 180° to about 210° C, under autogenous pressure.

The inventive process may be performed by the use of any conventional apparatus known in the art for providing a captive environment, such as sealable pressure vessels, autoclaves, and the like. Moreover, the resulting reaction product may be recovered by conventional procedures, e.g., precipitation and isolation by filtration, centrifugation, and the like. The process can be carried out either batch wise or in a continuous manner by employing selected conventional apparatus known in the art.

The particular time period the reactants are heated in the practice of my invention is not critical and is dependent upon the particular temperature employed, the concentration of reactants, the resultant yield of product desired and the like. Preferably, the mixture of reaction compounds is heated for a time period sufficient to effect a substantially quantitative yield of the corresponding novel compound. Normally, the time period of reaction is between about 2 to about 10 hours. A shorter period of time may be used if one is willing to accept a lower yield.

The particular amounts of reactant compounds are not critical, but it is preferred that the acetic acid be present in the reaction mixture in a molar excess to provide a substantially quantitative yield of product. Preferably, acetic acid is mixed and reacted with the polychlorobenzonitrile compound in a mole ratio ranging from about 2:1 to about 60:1 acetic acid:polychlorobenzonitrile compound. The especially preferred ranges are about 4 to about 30 moles acetic acid per mole polychlorobenzonitrile compound.

The following Examples illustrate individual preparations of the novel compounds of my invention but are not to be construed as limitative.

EXAMPLE I 27.5 grams pentachlorobenzonitrile and 200 ml. glacial acetic acid were charged to a 1.1 steel pressure vessel. Upon sealing the vessel, the mixture of reactants was heated at 190° C for 8 hours. The crude reaction mixture was then added to 1.5 l. of water and the resulting precipitate (25.4 gms., 75.9% yield) was isolated by filtration. Crystallization from chloroform afforded a white powder identified as N-acetyl-pentachlorobenzamide of the formula

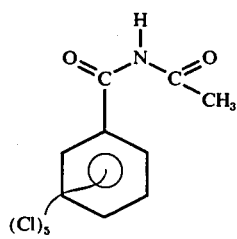

Identification of the compound was based on the following analytical and spectral data:

Analytical Data

Calculated for $C_9H_4Cl_5NO_2$ (molecular weight, 335.40): 52.86% Cl; 4.02% N. Found: 54.8% Cl; 4.0% N.

Spectral Data

Infrared Analysis (KBr disk, $cm^{-1}$): 3280 (m), 3190 (m), 1740 (vs), 1242 (vs). (m = medium intensity, vs = very strong intensity).

Mass Spectrum

High resolution mass spectral analysis definitively established the composition to be $C_9H_4Cl_5NO_2$ (prominent peaks were observed at m/e of 333 (p), 298, 275, 257, 247, 212, 177 and 142).

EXAMPLE II

In an attempt to prepare acetoxy-tetrachlorobenzonitrile by aromatic nucleophilic substitution reaction 30.0 gms. (0.11 mole) pentachlorobenzonitrile, 25.0 gms. (0.31 mole) sodium acetate, 200 ml. glacial acetic acid, and 100 ml. acetic anhydride were charged to a stainless steel autoclave. The mixture of reactants was heated at 190° C for 2 hours (autogenous pressure). The crude reaction mixture was then poured over water and the resulting light brown precipitate (17.0 gms.) was isolated by filtration. Most unexpectedly, upon analysis as set forth in Example I, the precipitate was shown to be an N-acetyl-pentachlorobenzamide.

EXAMPLE III

In a similar manner to the process of Example II, 30.0 gms. pentachlorobenzonitrile, 25.0 gms. sodium acetate, 200 ml. acetic acid and 100 ml. acetic anhydride were charged to a 1 l. stainless steel pressure vessel and heated for 4 hours at 190° C. The dark reaction mixture was then poured into water and filtered. After drying, the resulting solid, which was later proven to be N-acetyl-pentachlorobenzamide by analysis as set forth in Example I, had a weight of 35.5 gms. (97.3% yield).

EXAMPLE IV

The procedure of Example II was repeated except that the reactants were heated at 190° C for about 8 hours. In this manner there was isolated 33.5 gms. (91.0% yield) of a light tan solid shown to be N-acetyl-pentachlorobenzamide. A portion of this material was crystallized from chloroform; white powder, m.p. 208–210. Purification was also effected by sublimation (1 mm. at 160° C) and column chromatography (silica gel, heptane-chloroform).

EXAMPLE V

Into a 500 cc. three-neck flask was placed 7.0 gms. pentachlorobenzonitrile, 12.0 gms. sodium acetate, and 200 cc. dimethylsulfoxide. The resulting mixture was stirred under nitrogen for 4 hours at 130° C, then poured into 1500 cc. of water. Acidification of the aqueous solution with concentrated hydrochloric acid resulted in the appearance of a white solid material that was isolated by filtration. This solid was allowed to dissolve in ether and the resulting ether solution treated with magnesium sulfate. After removal of the solvent under reduced pressure, there remained 6.0 gms. of white crystalline solid that was subsequently shown to be hydroxy-tetrachlorobenzonitrile.

EXAMPLE VI 27.5 gms. hydroxy-tetrachlorobenzonitrile and 100 ml. acetic acid were mixed in a 1 l. stainless steel pressure vessel and allowed to react under autogenous pressure at 205° C for 5 hours. Upon isolation by cooling and filtration, the precipitate was shown by analysis to be N-acetyl-hydroxy-tetrachlorobenzamide of the formula

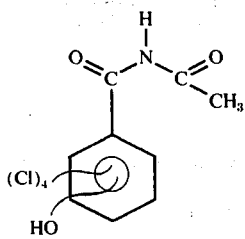

EXAMPLE VII

Hydroxy-tetrachlorobenzonitrile (58.0 gms.), acetic acid (200 ml.), and acetic anhydride (200 ml.) were heated in a 1 l. stainless steel autoclave at 190° C for 8 hours. Concentration in vacuo followed by addition of cold water afforded 61.0 gms. of a mixture containing N-acetyl-hydroxy-tetrachlorobenzamide and N-acetyl-acetoxy-tetrachlorobenzamide.

Elemental Analysis

Calculated for N-acetyl-hydroxy-tetrachlorobenzamide ($C_9H_5cl_4NO_3$) 44.8% Cl; Found 46.5% Cl.

Spectral Analysis

NMR: Absorption at 7.6 $\tau$

Infrared (nujol mull, $cm^{-1}$): 3290, 3220, 1800, 1750, 1238, 1190, 1040, 910, 730.

N-acetyl-acetoxy-tetrachlorobenzamide was readily converted to N-acetyl-hydroxy-tetrachlorobenzamide by acid hydrolysis.

EXAMPLE VIII

In a process similar to Example VI hydroxy-tetrachlorobenzonitrile (6.0 gms.) and acetic acid (85 ml.) were charged to a stainless steel autoclave and heated at 180° C for 3 hours. The interaction provided the formation of N-acetyl-hydroxy-tetrachlorobenzamide uncontaminated by N-acetyl-acetoxy-tetrachlorobenzamide.

EXAMPLE IX

When a mixture of pentachlorobenzonitrile (20.0 gms.), phosphoric acid (100 ml.) and acetic acid (100 ml.) was refluxed for 5 hours, only starting material was recovered.

The compounds of my invention are useful biological chemicals, particularly in controlling undesirable vegetation, which is illustrated by the data in the Tables below.

The data in Table 1 show N-acetyl-pentachlorobenzamide to be an excellent post-emergence herbicide while non-phytotoxic to wheat, oats, red kidney beans, milo and corn and cotton. The data in Table 2 show N-acetyl-pentachlorobenzamide to be a pre-emergence herbicide providing good control of pigweed and seteria (foxtail) without injury to milo or corn. Comparable results to those in the tables, below, may be obtained in testing other compounds within the scope of my invention.

POST EMERGENCE HERBICIDAL SCREEN TEST

The purpose of the test recorded in Table 1 was to make foliar application to a series of crops, under standard conditions, to evaluate the post-emergence herbicidal activity of N-acetyl-pentachlorobenzamide. The crops employed in this post-emergence herbicidal evaluation were pigweed, setaria (foxtail), Johnson grass, morning glory (of the bindweed family), milo, oats, wheat, red kidney beans, cotton and corn. The weed species were approximately 2 inches in height at time of spraying, corn about 4 inches and wheat and oats 3 inches. The red kidney beans were approximately 3 weeks old. The N-acetyl-pentachlorobenzamide was extended in water to obtain a desired final suspension. The compound was screened at 5 pounds per acre (active ingredient) calculated on a broadcast basis. Effective amounts range from 1 to 15 per pounds per acre. The plants were scored for phytotoxicity 10 to 12 days after spray application. Phytotoxicity ratings, set forth in the following Table 1, are based upon a scale of 0 to 10 in which 0 indicates no injury to the other extreme where 10 indicates that the plants were killed.

Table 1

| Post Emergence Herbicidal Evaluation of N-Acetyl-pentachlorobenzamide | | | | | |
|---|---|---|---|---|---|
| Dose lbs./Acre | Pigweed | Setaria | Johnson Grass | Morning Glory | Wheat |
| 5 | 10 | 5 | 2I | 7 | 0 |
| Dose lbs./Acre | Oats | Red Kidney Beans | Milo | Corn | Cotton |
| 5 | 0 | 0 | 0 | 0 | 0 |

I = INHIBITED

PRE EMERGENCE HERBICIDAL EVALUATION

The test recorded in Table 2 was conducted to determine herbicidal activity of N-acetyl-pentachlorobenzamide by a soil pre-emergence evaluation on 7 crops. Flats were planted to the desired crops to a depth of approximately ½ inch. The crops employed were pigweed, tomato, morning glory, Johnson grass, milo, seteria and corn. Care was employed in using a consistent amount of soil on the bottom of the flats, in the use of a template in the marking of the seed rows, in the amount of seeds used, and particularly in the amount of soil placed on top of the seeds in the interest of uniformity from day to day and test to test. The compound was initially screened at a dosage of 10 pounds of active ingredient per acre. Effective amounts range from 3 to 15 pounds per acre. The compound was extended in water and 250 ml. of such a suspension uniformly distributed over each flat. The flats were immediately transferred to a greenhouse and covered for a period of three days so that additional watering was not required until some of the plants had begun to make their appearance above ground. When it was assured that all emergence had occurred, as determined by the check, emergence counts were made on all crops. At the end of 14 to 16 days, a phytotoxicity reading was made on the various crops indicating the extent of damage not only to the stand of the crops, but also the extent of damage to the emerged seedlings. Phytotoxicity data set forth in the following Table 2 are recorded on a scale of 0 to 10 in which 0 indicated no injury to the other extreme where 10 indicates that the plants were killed.

Table 2

| Pre Emergence Herbicidal Evaluation Of N-Acetyl-pentachlorobenzamide |
|---|

Table 2-continued

| Dose lbs./Acre | Variable | Pig-weed | Setaria | Johnson Grass | Milo |
|---|---|---|---|---|---|
| 10 | % Emergence | 10 | 10 | 85 | 85 |
|  | P. R.* | 9 | 10 | 0 | 0 |

| Dose lbs./Acre | Variable | Morning Glory | Tomato | Corn |
|---|---|---|---|---|
| 10 | % Emergence | 85 | 30 | 85 |
|  | P. R.* | 0 | 9 | 0 |

*Phytotoxicity Rating

I claim:
1. A process for controlling the growth of undesirable vegatation which comprises applying to said vegetation a herbicidally effective amount of N-acetly-pentachlorobenzamide.

* * * * *